(12) United States Patent
Rue et al.

(10) Patent No.: US 10,347,463 B2
(45) Date of Patent: Jul. 9, 2019

(54) ENHANCED CHARGED PARTICLE BEAM PROCESSES FOR CARBON REMOVAL

(71) Applicant: FEI Company, Hillsboro, OR (US)

(72) Inventors: Chad Rue, Portland, OR (US); Joe Christian, Portland, OR (US); Kenny Mani, Beaverton, OR (US); Noel Thomas Franco, Hillsboro, OR (US)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 15/374,617

(22) Filed: Dec. 9, 2016

(65) Prior Publication Data

US 2018/0166272 A1 Jun. 14, 2018

(51) Int. Cl.

| | |
|---|---|
| *H01L 21/311* | (2006.01) |
| *H01J 37/305* | (2006.01) |
| *H01J 37/30* | (2006.01) |
| *H01L 21/02* | (2006.01) |
| *G01N 21/00* | (2006.01) |

(52) U.S. Cl.
CPC ............. *H01J 37/30* (2013.01); *G01N 21/00* (2013.01); *H01J 37/3056* (2013.01); *H01L 21/02046* (2013.01); *H01L 21/02057* (2013.01); *H01L 21/02068* (2013.01); *H01L 21/31122* (2013.01); *H01L 21/31138* (2013.01)

(58) Field of Classification Search
CPC ........... H01L 21/3065; H01L 21/02071; H01L 21/02085; H01L 21/31138; H01L 21/31122; H01L 21/02046; H01L 21/02068; H01L 21/02057; H01J 2237/3056; H01J 2237/3053; H01J 2237/006; H01J 2237/31479; H01J 37/30; H01J 37/3056; H01J 37/3053
See application file for complete search history.

(56) References Cited

U.S. PATENT DOCUMENTS

| | | |
|---|---|---|
| 3,489,797 A | 1/1970 | Koenig et al. |
| 3,822,296 A | 7/1974 | Beattie et al. |
| 5,104,684 A | 4/1992 | Tao et al. |
| 5,435,850 A | 7/1995 | Rasmussen |
| 5,851,413 A | 12/1998 | Casella et al. |

(Continued)

FOREIGN PATENT DOCUMENTS

| | | |
|---|---|---|
| CA | 783558 A | 4/1968 |
| FR | 1220575 A | 5/1960 |
| WO | 9526371 A1 | 10/1995 |

OTHER PUBLICATIONS

Giannuzzi, Lucille, et al., "Introduction to Focused Ion Beams: Instrumentation, Theory, Techniques and Practice," pp. 250-255, Chapter 12.

*Primary Examiner* — Michael M Trinh (57) ABSTRACT

Method and system for enhanced charged particle beam processes for carbon removal. With the method and system for enhancing carbon removal, associated method and system for decreasing levels of carbon impurity in depositions, also using a precursor gas in charged particle beam processes (and particularly focused ion beam methodologies), are provided. In a preferred embodiment, the precursor gas comprises methyl nitroacetate. In alternative embodiments, the precursor gas is methyl acetate, ethyl acetate, ethyl nitroacetate, propyl acetate, propyl nitroacetate, nitro ethyl acetate, methyl methoxyacetate, or methoxy acetylchloride.

13 Claims, 7 Drawing Sheets

(56) References Cited

U.S. PATENT DOCUMENTS

| | | | |
|---|---|---|---|
| 5,958,799 A | 9/1999 | Russell et al. | |
| 6,140,655 A | 10/2000 | Russell et al. | |
| 8,059,918 B2 | 11/2011 | Young et al. | |
| 8,076,650 B2 | 12/2011 | Smith et al. | |
| 8,358,832 B2 | 1/2013 | Young et al. | |
| 8,405,054 B2 | 3/2013 | Smith et al. | |
| 8,524,606 B2 * | 9/2013 | Charns | H01L 21/31053 216/37 |
| 8,692,217 B2 | 4/2014 | Smith et al. | |
| 8,781,219 B2 | 7/2014 | Warschauer et al. | |
| 9,029,812 B2 | 5/2015 | Smith et al. | |
| 9,064,811 B2 | 6/2015 | Rue et al. | |
| 9,087,366 B2 | 7/2015 | Young et al. | |
| 9,401,262 B2 | 7/2016 | Smith et al. | |
| 9,443,697 B2 | 9/2016 | Rue | |
| 2004/0256743 A1 | 12/2004 | Funaki et al. | |
| 2013/0248356 A1 * | 9/2013 | Rue | C23C 14/46 204/192.34 |
| 2014/0106559 A1 * | 4/2014 | Anderson | H01L 23/5256 438/601 |
| 2014/0357088 A1 * | 12/2014 | Rue | H01L 21/76892 438/723 |
| 2015/0294885 A1 | 10/2015 | Rue et al. | |

* cited by examiner

FIG. 6B
Surface after cleaning with Dx (≈ 5 sec)

FIG. 6A
Surface with carbon contamination

FIG. 7

ENHANCED CHARGED PARTICLE BEAM PROCESSES FOR CARBON REMOVAL

TECHNICAL FIELD

The present invention relates to the field of charged particle beam processes and, in particular, to method for enhancing carbon removal (including method for decreasing carbon impurity levels in depositions) using a precursor gas in such processes.

BACKGROUND

Charged particle beam processes, particularly focused ion beam (FIB) methodologies, support a broad range of scientific and technological applications. See: (1) L. A. Giannuzzi, F. A. Stevie, *Introduction to Focused Ion Beams: Instrumentation, Theory, Techniques, and Practice* (Springer, New York, 2005); and (2) J. Orloff, M. Utlaut, L. Swanson, *High Resolution Focused Ion Beams: FIB and Its Applications* (Kluwer Academic/Plenum Publishers, New York, 2003). Charged particle beam processes may be carried out in a variety of systems, including a FIB system, an electron beam system such as a scanning electron microscope (SEM) system, or a dual beam FIB/SEM system. For example, see (3) U.S. Pat. No. 8,059,918 (issued Nov. 15, 2011) to Young et al., "High accuracy beam placement for local area navigation," continuation U.S. Pat. No. 8,358,832, and continuation-in-part U.S. Pat. Nos. 8,781,219 and 9,087,366, each of which is herein incorporated by reference in its entirety.

A gas phase chemical precursor (a precursor gas) may be introduced, e.g., via a gas injection system (GIS), to enhance, suppress, or otherwise modify many of these various processes, such as the etching or milling of a sample, or the depositing on a sample of either a dielectric film {e.g., using, with or without an oxidizing agent (e.g., $H_2O$, $O_2$, or $N_2O$), a silicon-bearing precursor gas such as: 2, 4, 6, 8, 10, 12-hexamethylcyclohexasiloxane (HMCHS); 2, 4, 6, 8, 10-pentamethylcyclopentasiloxane (PMCPS); 2, 4, 6, 8-tetramethylcyclotetrasiloxane (TMCTS); or tetraethylorthosilicate (TEOS)} or a metal such as molybdenum (Mo), tungsten (W), or platinum (Pt) {e.g., using an organomolybdenum, an organotungsten, or an organoplatinum deposition gas such as, respectively: molybdenum hexacarbonyl [i.e., $Mo(CO)_6$], tungsten hexacarbonyl [i.e., $W(CO)_6$], or trimethyl(methylcyclopentadienyl)platinum(IV) [i.e., $C_5H_4CH_3Pt(CH_3)_3$ or $C_9H_{16}Pt$]. See also (4) U.S. Pat. No. 5,104,684 (issued Apr. 14, 1992) to Tao et al., "Ion beam induced deposition of metals," which is herein incorporated by reference in its entirety, and which discloses other precursor gases for the deposition of metals, including additionally for Pt deposition: $Pt(acetylacetonate)_2$; $Pt(PF_3)_4$; and $Pt(CO)_2Cl_2$.

Water vapor is an example of a precursor gas that may be used in charged particle beam processes to modify milling rates. More specifically, water vapor may act as an etch-assisting gas in gallium ion ($Ga^+$) FIB milling of carbonaceous compounds such as diamond or polyimide (as included in photoresist material). Use of water vapor may increase the etching rate by about seven times (7×) for diamond, or about twenty times (20×) for polyimide, over the default milling rate (defined as the milling rate without an etch-assisting gas), as described in (5) U.S. Pat. No. 5,958,799 (issued Sep. 28, 1999) to Russell et al., "Method for water vapor enhanced charged-particle-beam machining," which is herein incorporated by reference in its entirety. However, potentially deleterious implantation of gallium ions into a sample is largely unavoidable if the sample is milled or etched using a conventional $Ga^+$ FIB system. Consequently, use of alternative processes, such as xenon ($Xe^+$) plasma FIB (PFIB) methodologies (with reduced ion implantation), may be necessary.

In such a context, oxygen gas ($O_2$) may be used as an etch-assisting gas in $Xe^+$ PFIB milling of polyimide material (common in encapsulating material on integrated circuit (IC) package devices). For example, at somewhat low acceleration voltages (e.g., 8 keV to 14 keV) versus higher acceleration voltages (e.g., 30 keV), use of oxygen gas may increase etching in polyimide material to a rate that is more than twenty-five times (25×) a conventional milling rate (depending on the particular polyimide composition) as described in (6) U.S. Pat. No. 9,443,697 (issued Sep. 13, 2016) to Rue, "Low Energy Ion Beam Etch," which is herein incorporated by reference in its entirety. More specifically, U.S. Pat. No. 9,443,697 (col. 5, lns. 25-32) notes that a removal rate of about 9.8 $\mu m^3/nC$ may be obtained—using a $Xe^+$ PFIB beam at 8 keV and current density of 4 $pA/\mu m^2$ with a dwell time of 100 nsec, a 0% pixel overlap, and a chamber pressure (with the $O_2$ valve open) of $2 \times 10^{-5}$ Torr—versus etching polyimide material using a conventional approach (e.g., water-assisted etching using a $Xe^+$ PFIB beam at 30 keV), which results in a removal rate of only about 0.35 $\mu m^3/nC$. Despite these encouraging results, however, the highly volatile nature of oxygen gas may lead to inconsistent or highly variable outcomes.

Accordingly, it would be desirable further to enhance carbon removal from carbonaceous material in charged particle beam processes—but without needing to acquiesce in various disadvantages such as those noted above (i.e., gallium ion implantation into samples or, where oxygen is used as an etch-assisting gas in a PFIB system, potential highly variable outcomes for carbon removal from samples of carbonaceous material).

SUMMARY

The foregoing discussed drawbacks, as well as other deficiencies, are overcome or alleviated through the use, as described herein, of methyl nitroacetate (MNA) as a precursor gas in charged particle beam processes. That is, MNA may be used as a precursor gas markedly to enhance carbon removal from carbonaceous materials in charged particle beam processes.

Such beneficial use is surprisingly unexpected in view of the prior art use of MNA as a precursor gas being associated with suppressed etching rates for FIB milling of copper and low-k dielectric materials in ion-beam induced planar deprocessing of "mixed field materials" on IC devices. See (7) U.S. Pat. No. 9,064,811 (issued Jun. 23, 2015) to Rue et al., "Precursor for planar deprocessing of semiconductor devices using a focused ion beam," which is herein incorporated by reference in its entirety. As a result of this suppressed etching, the milling of different materials on IC devices may be accomplished at substantially similar rates, and a more uniform milling floor may be produced (see, for example, col. 5, lns. 21-32 of U.S. Pat. No. 9,064,811).

In view of such suppressed etching of copper and low-k dielectric materials in the context of planar deprocessing of mixed field materials on IC devices, the use of MNA as a precursor gas accordingly could be expected to reduce the etching rate in the milling of various materials (including potentially carbonaceous materials) in related charged particle beam processes. Surprisingly, however, applicant inventors have identified conditions under which MNA, or MNA-related chemical, may be used as a precursor gas markedly to enhance carbon removal from carbonaceous materials in charged particle beam processes. "MNA-related chemical" includes (nonexclusively) methyl acetate, ethyl acetate, ethyl nitroacetate, propyl acetate, propyl nitroacetate, nitro ethyl acetate, methyl methoxyacetate, methoxy acetylchloride, and similar chemical compounds containing short-chain hydrocarbons joined to acetate, nitro, or nitroacetate groups such that: (a) use of the chemical results in moderate vacuum chamber pressures in the range of about $2 \times 10^{-6}$ to about $5 \times 10^{-5}$ mbar [i.e., about $1.5 \times 10^{-6}$ to about $3.75 \times 10^{-5}$ Torr] while the precursor gas is flowing (and with the baseline chamber pressure when the chemical compound is not flowing being in the range of about $1 \times 10^{-7}$ to about $1 \times 10^{-6}$ mbar [i.e., about $7.5 \times 10^{-8}$ to about $7.5 \times 10^{-7}$ Torr]) for convenient delivery of the chemical into the FIB vacuum chamber (for a FIB implementation using MNA-related chemical); and (b) the chemical has an oxidizing capacity toward the sample, or, e.g., in the context of sample surface cleaning, toward contaminant molecules adsorbed onto the sample surface.

In recognition of the potential benefits of such use of MNA in charged particle beam processes for carbon removal from carbonaceous materials—such as diamond and polyimide materials, as previously noted, or plastics or organic resins comprising other carbon-rich polymer materials, e.g., polycarbonate, polyester, polyethylene, polypropylene, polystyrene, polyurethane, etc.—an object herein is to provide method for enhancing carbon removal using MNA, or MNA-related chemical, as a precursor gas in charged particle beam processes on such various carbonaceous materials. An organic resin comprising other carbon-rich polymer material may have a biological origin, e.g., originate from a biological sample.

The object of enhancing carbon removal through use of MNA as a precursor gas also includes decreasing carbon impurity levels in deposits generated through processes of charged particle beam deposition. For example, MNA, or MNA-related chemical, may be used as a precursor gas to reduce carbon impurities in metallic or dielectric deposits where those carbon impurities originate from carbon atoms in deposition precursor gas molecules (e.g., an organometallic gas for deposits of metal or, for dielectric deposits, a silicon-bearing deposition gas). This reduction in carbon impurities during charged particle beam deposition may be viewed as "preemptive carbon removal"—possibly through a carbon scavenging and volatilization mechanism.

Finally, in an implementation related to the object of enhancing carbon removal through use of MNA as a precursor gas, MNA, or MNA-related chemical, may be used as a precursor gas in cleaning surfaces through charged particle beam processes (e.g., to assist in removal of carbon-containing contaminants such as hydrocarbon residue from SEM sample surfaces).

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

One embodiment or implementation is directed to method for enhancing carbon removal using a precursor gas in ion-beam induced etching of carbonaceous substrates. For example, applicant inventors have found that carbon etching can be enhanced using an ion beam of low acceleration voltage in a PFIB system using MNA as the etching gas precursor.

A related embodiment or implementation is directed to method for decreasing levels of carbon impurity originating from organoplatinum deposition gas in ion beam-induced Pt deposition, including through, but not exclusively restricted to, the use of an ion beam of a low acceleration voltage in a PFIB system; use of a low keV ion beam is not required, although use of an ion beam of a relatively low acceleration voltage, e.g., 5-12 keV, may result in a smoother deposition texture. With a similar flexibility, applicant inventors note that, while much of the following description is directed toward carbon removal from carbonaceous substrates, as well as toward diminishing carbon impurity levels in Pt deposition (or deposition of other metals via use of MNA, or an MNA-related chemical, in conjunction with an organometallic deposition gas such as, for example, an organotungsten deposition gas in W deposition) in ion-beam induced processes, methods and associated materials disclosed and claimed herein could readily be utilized for the removal of other materials from other substrates, as well as for diminishing impurities of other materials in other deposited compounds, in charged particle beam processes (e.g., in, nonexclusively, either electron beam-induced processes or ion beam-induced processes). The techniques described herein can be used by themselves or in combination with other techniques. Hence, the scope of the present invention should not be limited simply to carbon removal from carbonaceous substrates, or diminishing carbon impurity levels in Pt deposition, in ion beam-induced processes.

One initial aspect of the techniques described herein is to provide method for enhancing carbon removal using a precursor gas in ion-beam induced etching of carbonaceous substrates, particularly in etching these substrates with an ion beam of low acceleration voltage in a PFIB system.

Ingenuity in accomplishing this initial aspect presents a related second (unexpectedly accomplishable) aspect—to provide method for decreasing levels of carbon impurity originating from organoplatinum (or organometallic) deposition gas in ion beam-induced deposition of Pt (or another metal such as W) including through, but not exclusively restricted to, the use of an ion beam of a low acceleration voltage in a PFIB system (although processes for carbon scavenging need not be restricted to low energy beams). This second aspect may be viewed as providing method for "preemptive carbon removal" during Pt deposition (or deposition of another metal). Simultaneously flowing the metal precursor gas and MNA (or MNA-related chemical) during deposition can be accomplished either with separate gas injectors or by co-flowing the outputs of separate chemical containers through a shared exit nozzle.

A third aspect related to the two above-noted aspects is to accomplish the methods of these two aspects in sequence without sample removal from a charged particle beam instrument (e.g., etching or milling of carbonaceous material followed by Pt deposition using an organoplatinum deposition gas, or the reverse, i.e., Pt deposition followed by etching or milling, again without requiring sample removal from a charged particle beam instrument). For example, a metal film may be deposited in one or more steps of a multi-step process within a PFIB system, and then, within that same PFIB system, be scanned in the presence of MNA, or MNA-related chemical, for carbon removal from that deposited metal film. A process of depositing a thin layer of metal film and then completing MNA-treatment of that deposited metal film could be repeated multiple times to achieve a metal layer of desired thickness and containing diminished levels of carbon. Method according to this third aspect may be accomplished using a multi-source PFIB system such as is described in (8) U.S. Pat. No. 8,076,650 (issued Dec. 13, 2011) to Smith et al., "Multi-source plasma focused ion beam system," and four continuation U.S. Pat. Nos. 8,405,054; 8,692,217; 9,029,812; and 9,401,262, each of which is herein incorporated by reference in its entirety.

Finally, in an implementation further related to the above-noted aspects, method is provided for cleaning surfaces via charged particle beam processes (e.g., to assist in removing carbon contaminants from SEM contaminated surfaces, whether contamination originated from carbon deposited by SEM irradiation or it accumulated during storage or in some other way).

TABLE 1

Abbreviations

| Abbreviation | Appositive |
|---|---|
| CAD | computer aided design |
| Dx | methyl nitroacetate precursor gas |
| EDX | energy dispersive X-ray |
| FIB | focused ion beam |
| GIS | gas injection system |
| IC | integrated circuit |
| MNA | methyl nitroacetate |
| PFIB | plasma focused ion beam |
| SEM | scanning electron microscope |

In some embodiments or implementations, method of chemically-enhanced charged particle beam milling of a work piece area is described, the method comprising: providing an etch-assisting gas to a surface of the work piece area targeted for milling, wherein at least a portion of the surface of the targeted work piece area consists essentially of carbonaceous material; directing a focused ion beam toward the portion of the surface that consists essentially of carbonaceous material, thereby removing carbon from the targeted area; in which: the etch-assisting gas comprises a chemical selected from a group consisting of methyl nitroacetate, methyl acetate, ethyl acetate, ethyl nitroacetate, propyl acetate, propyl nitroacetate, nitro ethyl acetate, methyl methoxyacetate, and methoxy acetylchloride; and the carbonaceous material is selected from the group consisting of diamond, vitreous carbon, polyimide material, and organic resin comprising other carbon-rich polymer material. For related methods, described are focused ion beam originating from a plasma focused ion beam source; ions of the focused ion beam being selected from the group consisting of: $Xe^+$, $Ar^+$, $Kr^+$, $O^+$, $O_2^+$, $N^+$, $N_2^+$, $NO^+$, and $NO_2^+$; focused ion beam operating during carbon removal at a very low or low acceleration voltage ranging from about 2 keV to about 14 keV; etch-assisting gas chemical being or comprising methyl nitroacetate; and/or carbon-rich polymer material being selected from the group consisting of polycarbonate, polyester, polyethylene, polypropylene, polystyrene, and polyurethane.

In some embodiments or implementations, method of charged particle beam chemical vapor deposition of a metallic film on a work piece surface area is described, the method comprising: providing an organometallic deposition gas to the work piece surface area targeted for deposition of the metallic film; providing a carbon-removal precursor gas to the work piece surface area targeted for deposition of the metallic film; directing a focused ion beam toward the work piece surface area targeted for deposition of the metallic film, thereby depositing the metallic film on the targeted work piece surface area; in which: the carbon-removal precursor gas comprises a chemical selected from a group consisting of methyl nitroacetate, methyl acetate, ethyl acetate, ethyl nitroacetate, propyl acetate, propyl nitroacetate, nitro ethyl acetate, methyl methoxyacetate, and methoxy acetylchloride. For related methods, described are organometallic deposition gas being selected from the group consisting of an organomolybdenum, an organotungsten, or an organoplatinum deposition gas; organometallic deposition gas being an organoplatinum deposition gas; focused ion beam originating from a plasma focused ion beam source; ions in the focused ion beam being selected from the group consisting of: $Xe^+$, $Ar^+$, $Kr^+$, $O_+$, $O_2^+$, $N^+$, $N_2^+$, $NO^+$, and $NO_2^+$; focused ion beam operating during deposition of the metallic film at an acceleration voltage ranging from about 2 keV to about 30 keV, or at an acceleration voltage ranging from about 2 keV to about 14 keV; and/or carbon-removal precursor gas being or comprising methyl nitroacetate.

In some embodiments or implementations, method of charged particle beam cleaning of a surface contaminated with carbon or hydrocarbon material is described, the method comprising: providing a carbon-removal precursor gas to a surface area targeted for cleaning; directing a charged particle beam toward the surface area targeted for cleaning, thereby removing carbon or hydrocarbon contaminant material from the surface; in which: the carbon-removal precursor gas comprises a chemical selected from a group consisting of methyl nitroacetate, methyl acetate, ethyl acetate, ethyl nitroacetate, propyl acetate, propyl nitroacetate, nitro ethyl acetate, methyl methoxyacetate, and methoxy acetylchloride. For related methods, described are charged particle beam being a focused ion beam; focused ion beam originating from a plasma focused ion beam source; ions originating from the plasma focused ion beam source being selected from the group consisting of: $Xe^+$, $Ar^+$, $Kr^+$, $O^+$, $O_2^+$, $N^+$, $N_2^+$, $NO^+$, and $NO_2^+$; plasma focused ion beam operating during surface cleaning at an acceleration voltage ranging from about 2 keV to about 30 keV, or at an acceleration voltage ranging from about 2 keV to about 5 keV; and/or ions originating from the plasma focused ion beam source being $Xe^+$ ions.

Not all aspects described above will be present in every embodiment or implementation of the invention.

Figure 1:
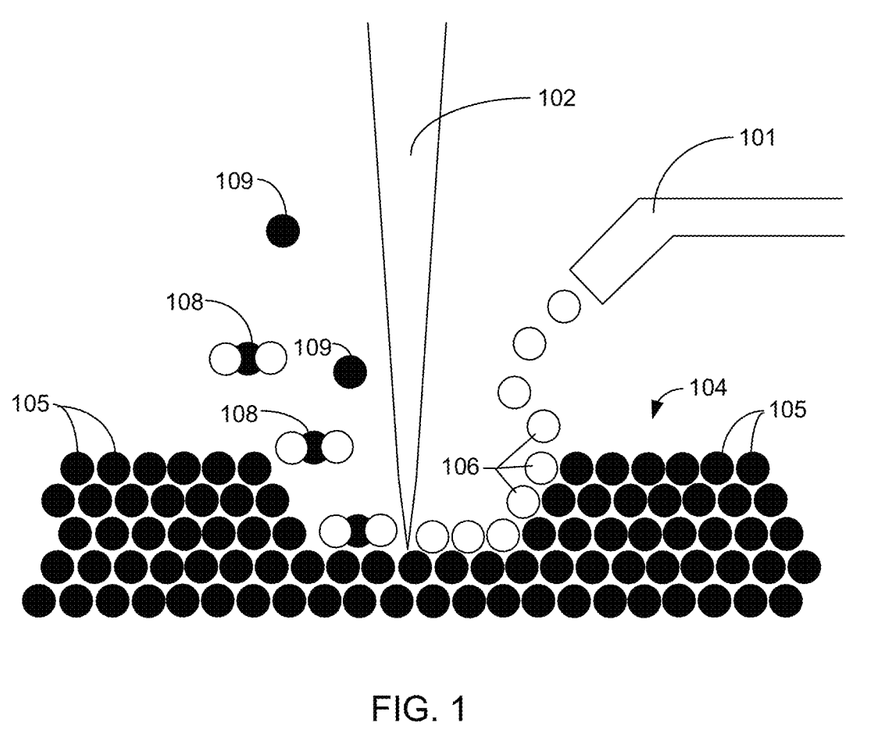
FIG. 1 is a schematic illustration of a typical FIB-mediated etching process using an etch-assisting gas.

FIG. 1 is a schematic illustration of a typical FIB-mediated etching process using an etch-assisting gas wherein ion beam 102 of the FIB system is used to process a work piece. Material removal in FIB systems may be accomplished by using beams of relatively large ions to physically sputter away material from a work piece 104. Sputtering by a FIB system may be further enhanced by using an etching gas (often referred to as a precursor gas) that is introduced near to the work piece surface through gas delivery nozzle 101 so that gas molecules 106 are adsorbed onto the surface.

Scanning the ion beam 102 over the defined area deposits energy into the substrate surface, i.e., induces enhanced local phonon densities. These phonons are believed to activate (or "crack") the adsorbed molecules 106 of the precursor gas, possibly in conjunction with secondary electrons induced by ion beam 102. These activated adsorbed molecules 106 then react with surface molecules 105 to promote etching of the underlying surface. Volatile reaction products 108 then leave the surface, along with some surface molecules 109 removed by sputtering. Some etching gases may spontaneously react with the work piece surface (i.e., no activation from the ion beam may be necessary).

Without being bound by an underlying theory on how use of MNA as a precursor gas enhances carbon removal in charged particle beam processes, it is possible that the oxidative nature of MNA, or MNA-related chemical, likely facilitates the chemical's adsorption to, and the formation of volatile reaction products with, carbonaceous material. Formation of volatile CO and $CO_2$ is likely, where the carbon atom originates from the substrate material, and the oxygen atom(s) originate from the MNA molecule. Nonetheless, the physics behind why MNA is effective is yet being investigated, and is not yet well-understood. But the theories described herein represent applicant's understanding of how various embodiments or implementations function, and these theories are presented to assist a skilled person in extending the examples described herein to other embodiments or implementations. Nevertheless, the empirical observations of MNA effectiveness as a precursor gas for carbon removal in charged particle beam processes (e.g., in etching polyimide, or in reducing carbon impurity levels in Pt deposition, with xenon ($Xe^+$) PFIB systems) are incontrovertible regardless of the correctness of applicant's understanding of the underlying theory.

Figure 2:
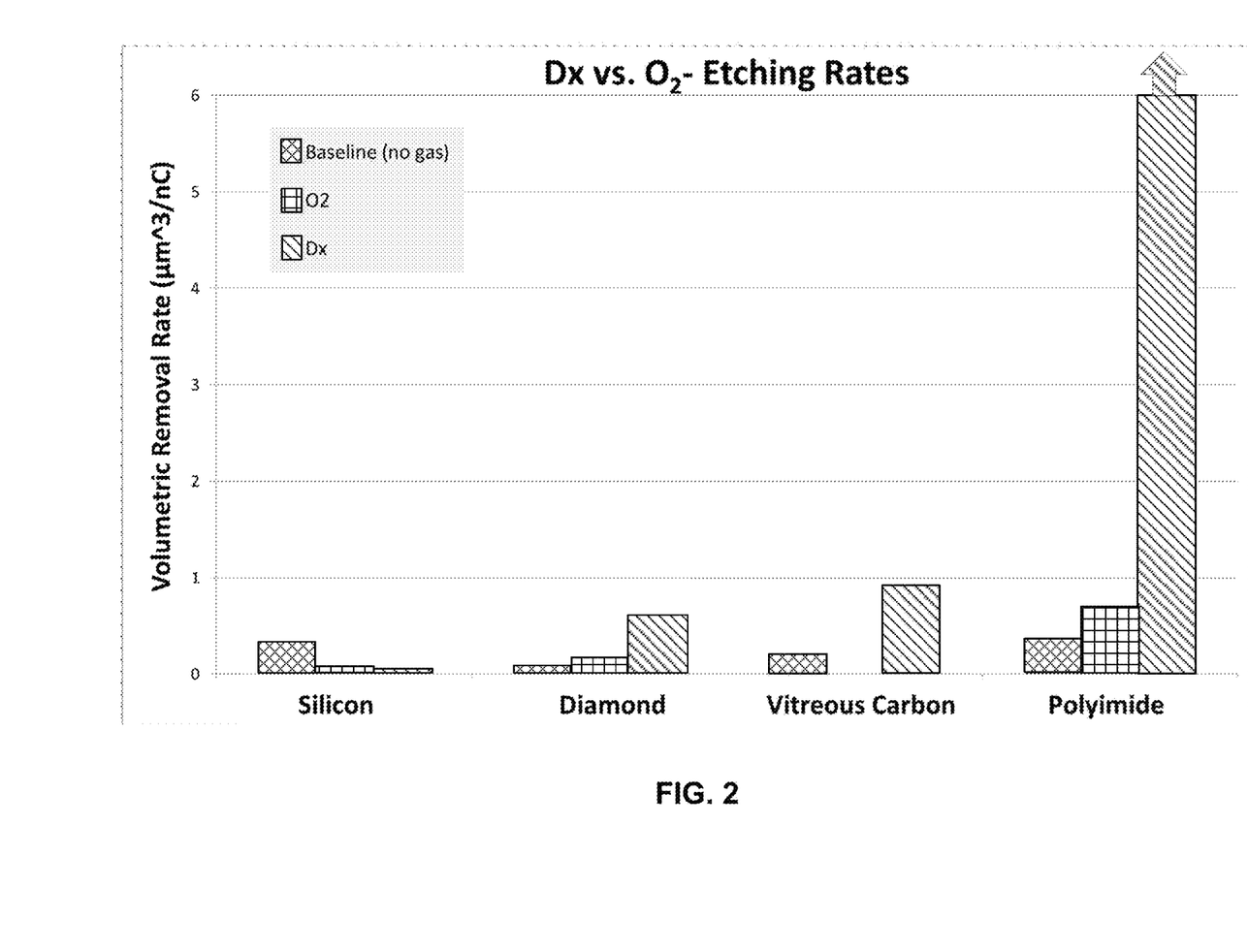
FIG. 2 is a bar graph of etching rate in silicon and three carbonaceous materials (diamond, vitreous carbon, and polyimide) under three separate conditions related to etch-assisting gas: no gas; oxygen gas ($O_2$); and MNA gas (Dx).

FIG. 2 is a bar graph that illustrates etching rate in silicon and three carbonaceous materials (diamond, vitreous carbon, and polyamide) under three separate conditions for etch-assisting precursor gas: no gas, oxygen gas (O2), and MNA gas (Dx). As the bar graph of FIG. 2 illustrates, use of Dx as a precursor gas for etching polyimide material with ion beams of low acceleration voltages (e.g., 12 keV) in a $Xe^+$ PFIB system results in enhanced removal of carbonaceous material (i.e., enhanced carbon removal) from each of the diamond, vitreous carbon, and polyamide materials—as compared to carbon removal using oxygen as etch-assisting gas (or as compared to foregoing the use of any such gas, e.g., under "no gas" baseline conditions as noted more specifically below). As this bar graph also illustrates, neither oxygen gas nor Dx gas enhances silicon removal. As indicated above, Dx (i.e., MNA gas) is known to inhibit milling on $SiO_2$ and metal substrates.

More specifically, $Xe^+$ PFIB beam parameters used for oxygen gas tests and Dx gas tests of FIG. 2 are: 12 keV acceleration voltage; 3.7 nA current; 100 nsec dwell time; 50% pixel overlap; and 5 pA/$\mu m^2$ current density—and $Xe^+$ PFIB beam parameters used for "no gas" baseline tests are: 30 keV acceleration voltage; 6.8 nA current; 1 μsec dwell time; 50% pixel overlap; and, again, 5 pA/$\mu m^2$ current density (i.e., the beam pattern size for "no gas" baseline tests was adjusted to keep the current density constant at 5 pA/$\mu m^2$ for all tests). For oxygen gas tests and Dx gas tests, the chamber pressure while gas was flowing was about $1 \times 10^{-5}$ mbar [i.e., about $7.5 \times 10^{-6}$ Torr]. For Dx gas tests, the "off the chart" etching rate in FIG. 2 for polyimide was observed to be about 9.9 $\mu m^3$/nC, with even higher etching rates being observed in Dx gas tests at current densities of less than 5 pA/$\mu m^2$ (see Table 2 and various removal rates in polyimide under beams at 12 keV acceleration voltage and 1.0 nA current with beam pattern size being adjusted to obtain the listed current densities).

TABLE 2

Additional Etching Rates in Polyimide with Dx Gas

| Current Density (pA/$\mu m^2$) | Removal Rate ($\mu m^3$/nC) |
|---|---|
| 40 | 1.51 |
| 10 | 4.08 |
| 4.4 | 9.52 |
| 2.5 | 11.65 |
| 1.11 | 14.75 |
| 0.625 | 15.24 |
| 0.40 | 16.10 |
| 0.28 | 16.36 |

With the use of either water vapor or oxygen as an etch-assisting gas, the effectiveness of etching polyimide material proved to be quite variable (data not shown). This variability in the case of oxygen may be attributable to a need for high surface flux for sufficient coverage with oxygen gas—a condition that is particularly challenging in view of the previously noted high volatility of oxygen gas. In contrast, using Dx as an etch-assisting gas generated consistent results. Furthermore, as indicated in FIG. 2 and above, these results include the removal of polyimide material with the use of Dx as an etch-assisting gas at a rate more than thirty times (30×) the rate of removal when no etch-assisting gas was used.

Figure 3:
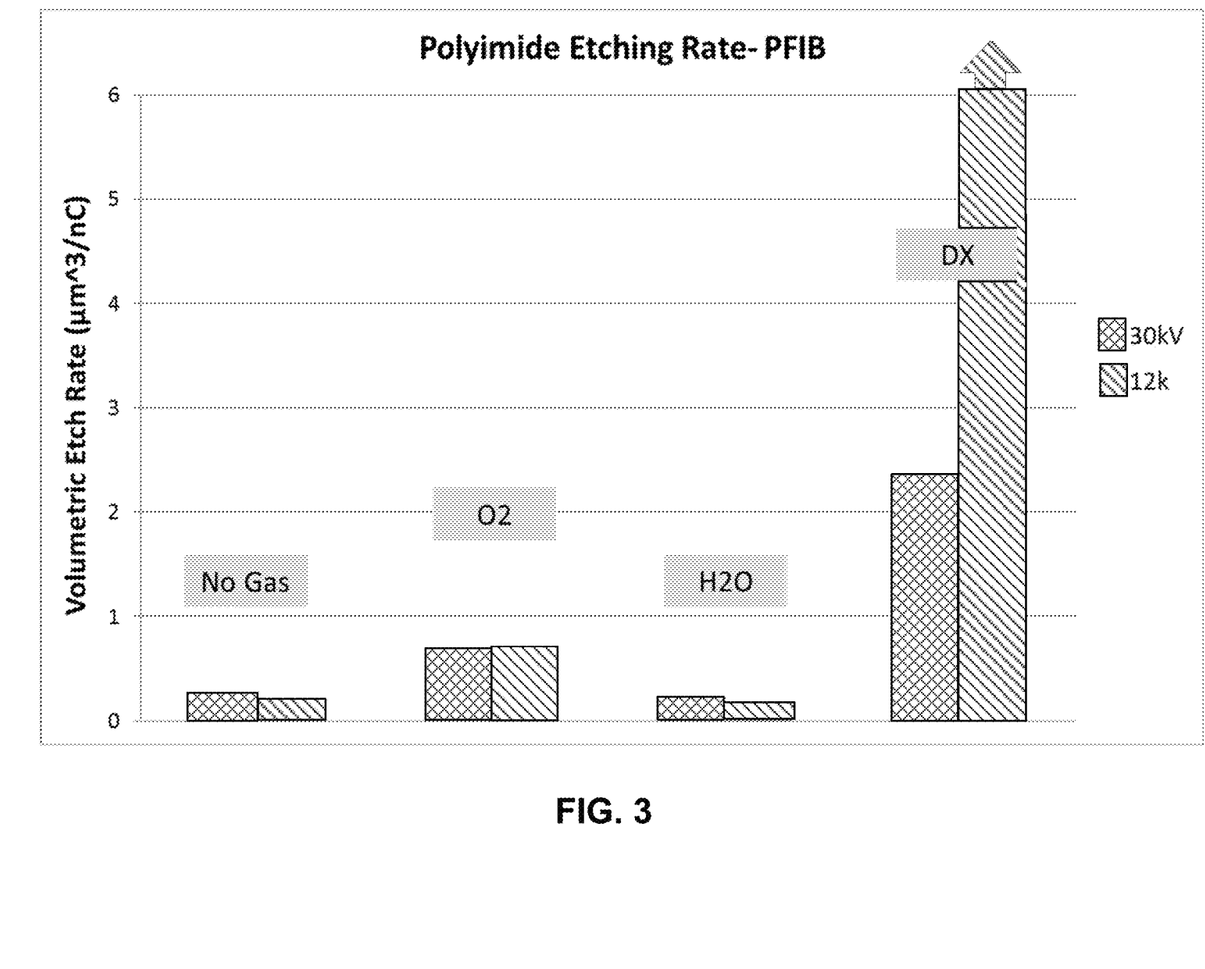
FIG. 3 is a bar graph of etching rate of a polyimide substrate using PFIB ion beam at acceleration voltages of about 30 keV (left) versus about 12 keV (right) under four conditions related to etch-assisting gas: no gas; oxygen gas ($O_2$); water vapor ($H_2O$); and MNA gas (DX).

FIG. 3 is a bar graph of etching rate of a polyimide substrate using a $Xe^+$ ion beam of a PFIB system at a low acceleration voltage of about 12 keV versus a higher acceleration voltage of about 30 keV under four separate conditions related to etch-assisting gas: "No Gas"; oxygen gas ("$O_2$"), water vapor ("$H_2O$"), and MNA gas ("DX")—with additional conditions as noted more specifically below. Etching rates are little changed for a PFIB system at a low acceleration voltage of about 12 keV versus at the higher acceleration voltage of about 30 keV for the etch-assisting gas conditions of no gas, oxygen gas, and water vapor. However, a four-times (4×) increase in removal rate results on using Dx gas in a PFIB system with the ion beam at the low acceleration voltage of about 12 keV over using Dx gas in a PFIB system with the ion beam at the higher acceleration voltage of about 30 keV. More specifically, the volumetric removal rate of polyimide material is about 10 $\mu m^3$/nC at the low acceleration voltage of about 12 keV (i.e., "off the chart" as indicated in FIG. 3), while, as further illustrated in FIG. 3, the removal rate is less than 2.5 $\mu m^3$/nC at the higher acceleration voltage of about 30 keV.

More specifically for FIG. 3, for the etch-assisting gas conditions of oxygen gas, water vapor, and Dx gas, beam parameters used again are: 100 nsec dwell time and 50% pixel overlap with chamber pressure while gas was flowing being about $1 \times 10^{-5}$ mbar [i.e., about $7.5 \times 10^{-6}$ Torr]; for the "no gas" condition, beam parameters used are 1 μsec dwell time and 50% pixel overlap settings. For tests at acceleration voltages of 12 keV, current settings used are 3.7 nA, and for tests at acceleration voltages of 30 keV, current settings used are 6.8 nA; but, for all tests of FIG. 3, beam pattern sizes are again adjusted to maintain current density at 5 pA/μm².

Figure 4A:
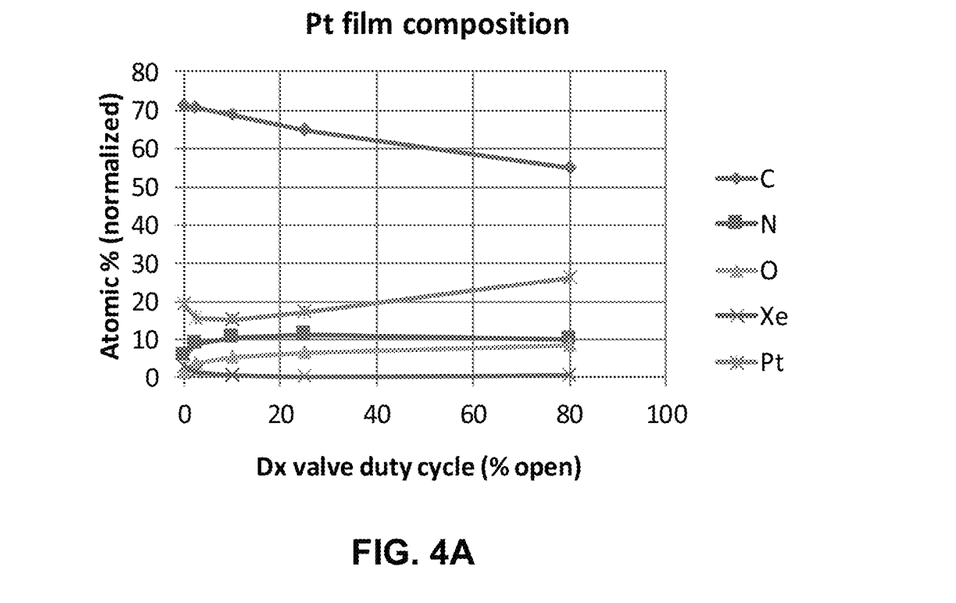
FIGS. 4a-4b provide two graphs that, for ion beam-induced Pt deposition, depict relationships between increasing availability of Dx gas and: (a) Pt film composition (FIG. 4a); and (b) Pt deposition growth rate (FIG. 4b).
Figure 4B:
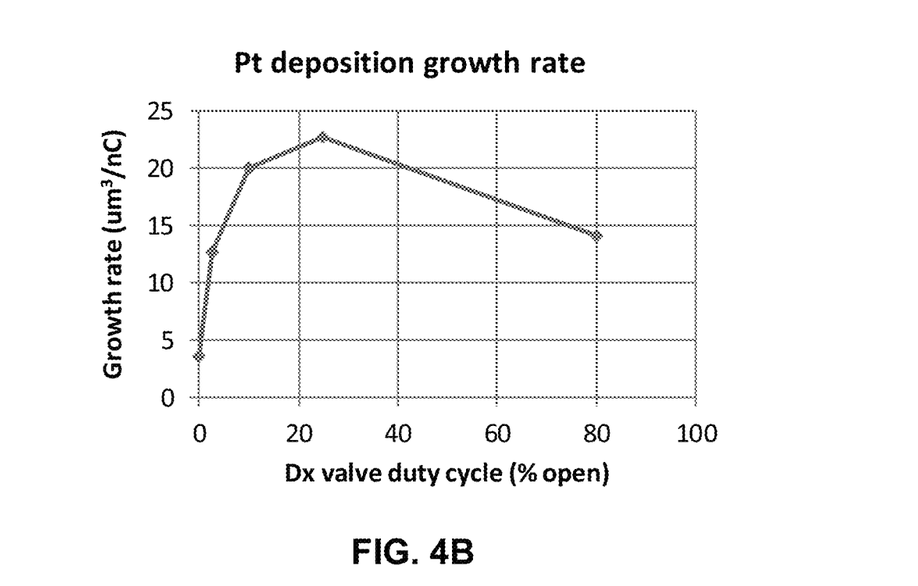

FIGS. 4a-4b provide two graphs that, for ion beam-induced deposition of platinum (Pt) with increasing availability of Dx gas, depict more specifically the following—

FIG. 4a: Pt film composition, wherein the top line depicts carbon impurity levels originating from organoplatinum deposition gas, illustrating that carbon levels in Pt film markedly decrease with increasing Dx gas availability and that this decrease in carbon levels is on an approximately linear track—the carbon levels being, as derived from this linear track, from about 69, 70, 71, or 72 atomic (mole) percent (normalized) when a GIS valve duty cycle for Dx gas insertion is set to be about 5% open, to about 65, 66, 67, or 68 atomic (mole) percent (normalized) when Dx gas insertion valve is set to be about 20% open, to about 61, 62, 63, or 64 atomic (mole) percent (normalized) when Dx gas insertion valve is set to be about 40% open, to about 57, 58, 59, or 60 atomic (mole) percent (normalized) when Dx gas insertion valve is set to be about 60% open, and to about 53, 54, 55, or 56 atomic (mole) percent (normalized) when Dx gas insertion valve is set to be about 80% open; in short and advantageously, with increased availability of Dx gas, carbon impurity levels decrease in Pt deposits; and FIG. 4b: Pt deposition growth rate (μm³/nC), wherein Pt deposition growth rate increases in an inverted parabolic manner from about 4 μm³/nC when a GIS valve duty cycle for Dx gas insertion is closed to a maximum growth rate of more than 22 μm³/nC when Dx gas insertion valve is set to be about 25% open, after which the Pt deposition growth rate decreases to about 14 μm³/nC when Dx gas insertion valve is set to be about 80% open.

Figure 5:
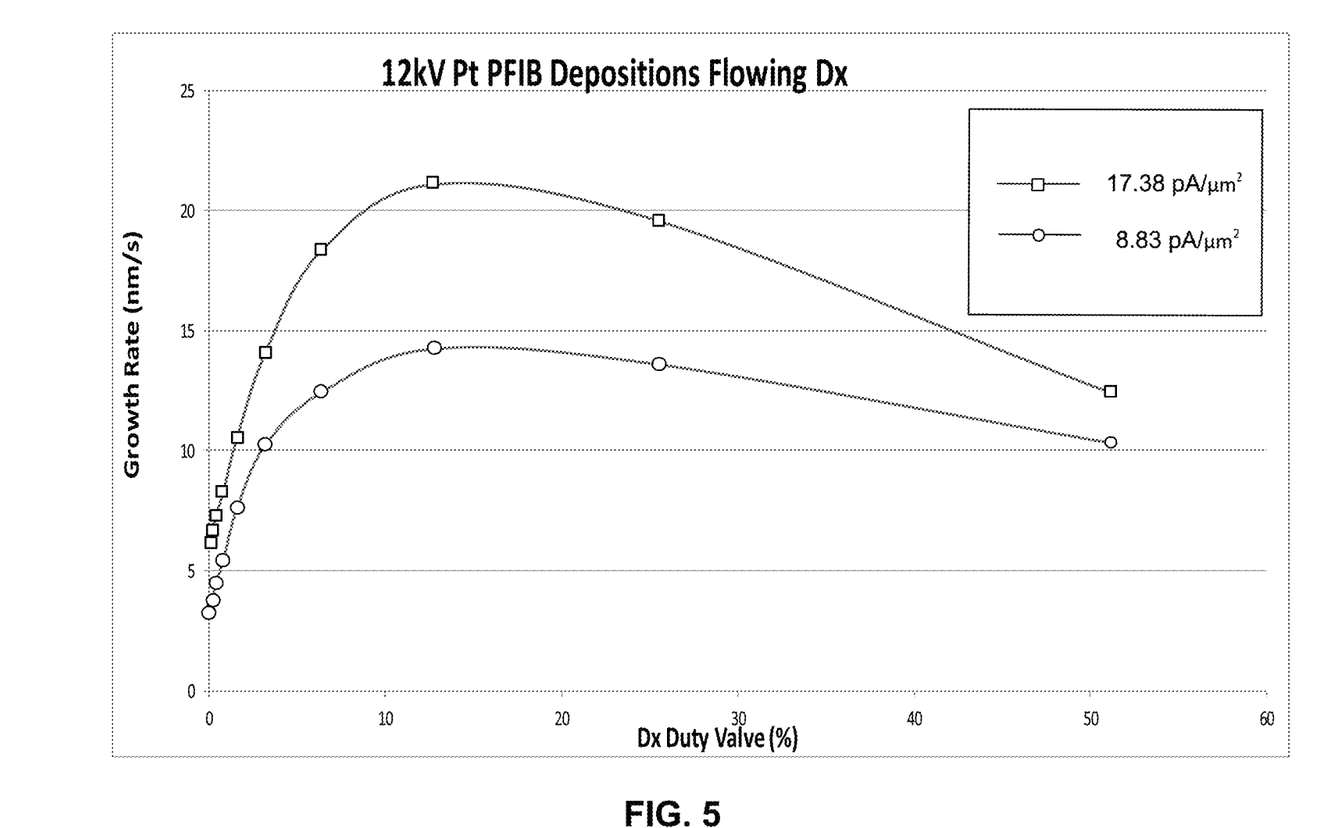
FIG. 5 is a graph illustrating Pt deposition enhancement under two different current densities with increasing Dx gas availability.

FIG. 5 is a graph illustrating Pt deposition growth rates under two different current densities with increasing Dx gas availability. More specifically, FIG. 5 illustrates that, at "high" current density (e.g., 17.38 pA/μm²), Pt deposition growth rate increases from about 6 nm/sec when a GIS valve duty cycle for Dx gas insertion is closed (i.e., the "no Dx gas" setting) to about 21 nm/sec when the Dx gas insertion valve is set to be about 15% open, which represents an increase of about three-and-one-half times (3.5×) Enhancement of the Pt deposition growth rate also occurs at a "low" current density. That is, at "low" current density of 8.83 pA/μm² and the same acceleration voltage, Pt deposition growth rate increases from about 3 nm/sec at the "no Dx gas" setting to about 14 nm/sec when the Dx gas insertion valve is set to be about 15% open, which represents an increase of about four-and-one-half times (4.5×).

FIG. 5 further illustrates that the Pt deposition growth rate remains well above the initial Pt deposition growth rate (i.e., the growth rate at the "no Dx gas" setting) when a GIS valve duty cycle for Dx gas insertion is further opened to a setting beyond 50% open. Specifically, for "high" current density of 17.38 pA/μm² and "low" current density of 8.83 pA/μm², the Pt deposition growth rate is about 12 nm/sec (up from about 6 nm/sec) and 10 nm/sec (up from about 3 nm/sec), respectively, when a GIS valve duty cycle for Dx gas insertion is set to be more than 50% open (versus the Pt deposition growth rate at the "no Dx gas" setting). In other words, although the increased availability of Dx gas passes an optimal availability for Pt deposition growth rates when a GIS valve duty cycle for Dx gas insertion is further opened beyond about 15% open, the increased availability of Dx gas at settings beyond 50% open yet results in Pt deposition growth rate increases of about two times (2×, i.e., to 12 nm/sec, up from the initial "no Dx gas" rate of about 6 nm/sec) for the "high" current density of 17.38 pA/μm², and of more than three times (3×, i.e., to 10 nm/sec, up from the initial "no Dx gas" rate of about 3 nm/sec) for the "low" current density of 8.83 pA/μm².

EDX (energy dispersive X-ray) analyses of Pt deposits confirm that Pt content in deposits is largely increased (and carbon impurity levels are substantially decreased) with increasing ratios of Dx gas concentration to Pt deposition gas concentration (i.e., [Dx gas]-to-[Pt deposition gas] ratios)—as indicated particularly in FIG. 4a. However, as indicated in FIG. 4b and as detailed in FIG. 5, Pt deposition growth rates slow at [Dx gas]-to-[Pt deposition gas] ratios beyond those ratios obtained when a GIS valve duty cycle for Dx gas insertion is set to be about 15% to 25% open (although Pt deposition growth rates under higher ratio conditions yet apparently remain well above "no Dx gas" Pt deposition growth rates).

More specifically for FIGS. 4b and 5, additional Xe⁺ PFIB beam parameters used for these depositions are: 12 keV acceleration voltage; 100 nsec dwell time; and 50% pixel overlap—similar Xe⁺ beam conditions were used for depositions accomplished for tests reported in FIG. 4a Chamber pressure changed slightly during the experiments as Dx gas flow rate was adjusted. In addition, instead of either the "high" current density of 17.38 pA/μm² or the "low" current density of 8.83 pA/μm² used for the tests reported in FIG. 5, an intermediate current density of about 10 pA/μm² is used for tests reported in FIG. 4b.

Figure 6A:
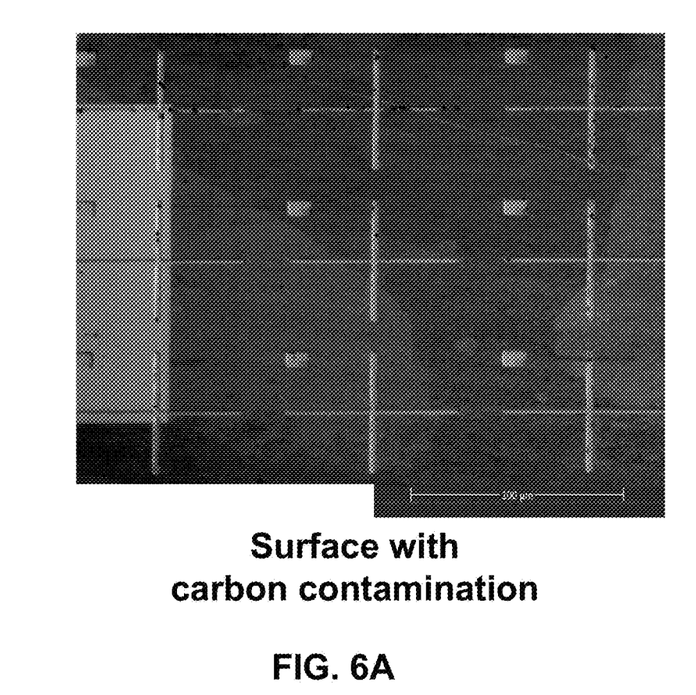
FIG. 6A and FIG. 6B provide two micrographs depicting a surface with carbon contamination (FIG. 6A) and the same surface after charged particle beam cleaning with Dx gas (FIG. 6B).
Figure 6B:
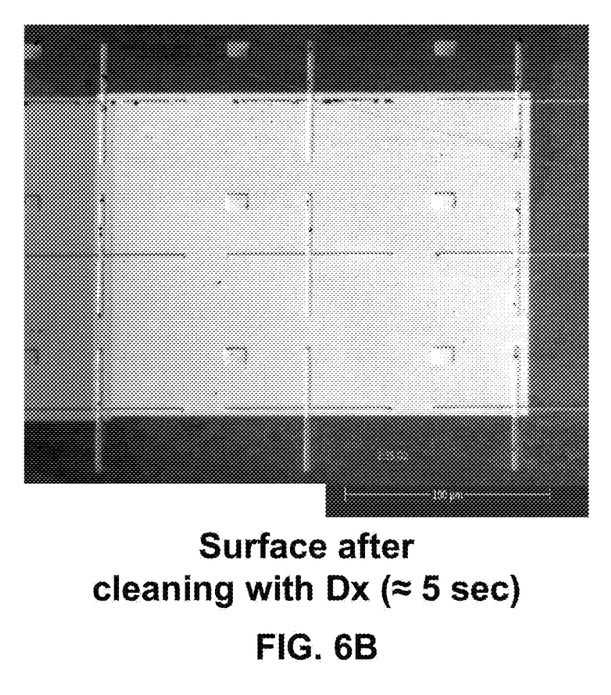

FIG. 6 depicts SEM micrograph of a dirty surface (left) and the same surface after charged particle beam cleaning (for about 5 seconds) (right) with Dx precursor gas in a Xe⁺ PFIB system. The surface area cleaned in the "Surface after cleaning with Dx (≈5 sec)" image (right) of FIG. 6 measures about 200 μm×200 μm (note: the SEM image of FIG. 6 is from a tilted perspective). More significant surface areas (e.g., 1 mm×1 mm) can be cleaned of carbon or hydrocarbon contamination (e.g., a surface dirtied by fingerprint oils, outgassing from plastic components, lubrications, solvents, etc.). through the use of large scan motions or stage movements—all without removing the sample from the instrument chamber. Dozens of cycles of such contamination removal (i.e., carbon or hydrocarbon removal) may be accomplished at very low acceleration voltage (e.g., 2-5 keV) or potentially higher energies without any discernable surface damage. In general, typical gas-assisted conditions may be used for cleaning, i.e., relatively low to moderate current densities (e.g., 5-20 pA/μm²), a short dwell time (e.g., 100 nsec), a moderate pixel overlap (e.g., between 0 and 50%), and a chamber pressure of approximately $2 \times 10^{-5}$ mbar when the chemistry is flowing.

Most FIB-based techniques for cleaning surfaces use oxygen or water vapor as a precursor gas, and ions at higher acceleration voltages (e.g., 12-30 keV), to remove contaminant films, and, consequently, considerable sputtering damage to a sample may occur. Also, commercial plasma cleaners operate on very large areas (the whole vacuum chamber, typically) and take a long time to execute and recover—e.g., at least several minutes. In contrast, conditions noted herein (e.g., using MNA, or MNA-related chemical, as precursor gas, and ions at, optionally but not restrictively, very low acceleration voltages, such as 2-5 keV, even though use of ions at higher acceleration voltages, e.g., 12-30 keV, may be workable for cleaning surfaces in some contexts) are effective, rapid (e.g., accomplishable in seconds), and avoid or minimize sputtering damage. In short, such use of MNA, or MNA-related chemical, as a precursor gas for surface cleaning in low-energy charged particle beam processes provides a needed alternative to time-consuming methods of plasma cleaning. That is, more effective cleaning over a region of interest may be provided, and, if needed, a user can confirm contamination removal through associated FIB or SEM processes.

Figure 7:
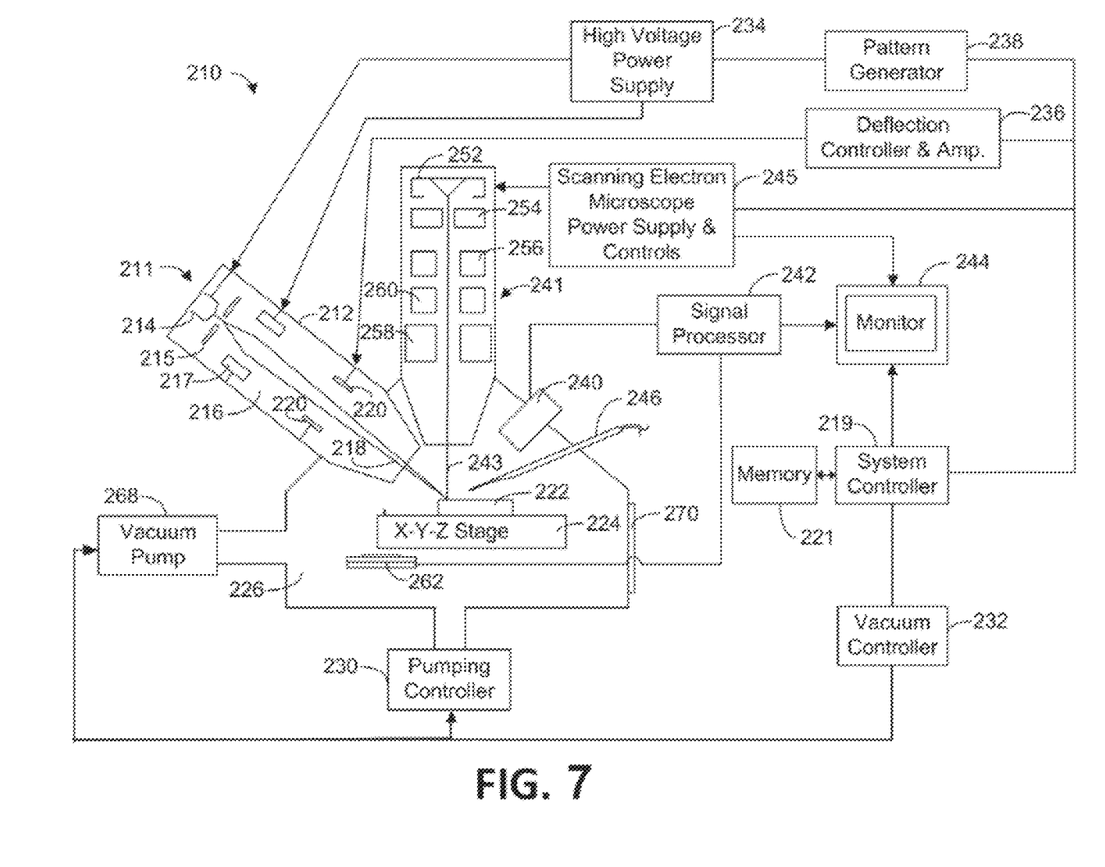
FIG. 7 shows a typical dual beam FIB/SEM system that could be used to implement aspects of the present invention.

FIG. 7 shows a typical dual beam FIB/SEM system 210 that could be used in implementations of aspects of the present invention. One implementation utilizes a dual beam FIB/SEM system 210 that uses an ion beam that is either normal or tilted by a few degrees to the plane of the sample surface and an electron beam having an axis that is also tilted, e.g., 52 degrees from the axis of ion beam. In some implementations, the ion beam and electron beam are capable of aligning so that the fields of view of both beams are coincident to within a few microns or less. The ion beam is typically used to image and machine the work piece, and the electron beam is used primarily for imaging but can also be used for some modification of the work piece. The electron beam will typically produce an image of a higher resolution than the ion beam image, and it will not damage the viewed surface like the ion beam. The image formed by the two beams can look different, and the two beams can therefore provide more information than a single beam.

Such a dual beam system could be made from discrete components or alternatively, could be derived from a conventional device such as an Expedia™ or a Helios Nano-Lab™ or a Scios™ or a Versa 3D DualBeam™ system—available from Thermo Fisher Scientific Company. Implementations using other particle beam systems, including for example, single beam systems, such as FIB or SEM only systems, or dual beam systems having two FIB columns, may also be useful.

Focused ion beam system 210 includes an evacuated envelope 211 having an upper neck portion 212 within which are located an ion source 214 and a focusing column 216 including extractor electrodes 215 and an electrostatic optical system 217. Ion beam 218 passes from ion source 214 through column 216 and between electrostatic deflection means schematically indicated at 220 toward sample 222, which comprises, for example, a semiconductor device positioned on movable X-Y-Z stage 224 within lower chamber 226. An ion pump or other pumping system (not shown) can be employed to evacuate neck portion 212. The chamber 226 is evacuated with turbomolecular and mechanical pumping system 268 under the control of vacuum controller 232. The vacuum system provides within chamber 226 a vacuum of between, e.g., approximately $1\times10^{-7}$ Torr and $5\times10^{-4}$ Torr. If an etch assisting, an etch retarding, or a deposition precursor gas is used, the chamber background pressure may rise, e.g., to about $1\times10^{-5}$ Torr.

High voltage power supply 234 is connected to ion source 214 as well as to appropriate electrodes in focusing column 216 for forming an ion beam 218 and directing the same downwardly. Deflection controller and amplifier 236, operated in accordance with a prescribed pattern provided by pattern generator 238, is coupled to deflection plates 220 whereby beam 218 may be controlled to trace out a corresponding pattern on the upper surface of sample 222. In some systems the deflection plates are placed before the final lens, as is well known in the art.

The ion source 214 typically provides a metal ion beam of gallium, although other ion sources, such as a multicusp or other plasma ion source, can be used. The ion source 214 typically is capable of being focused into a sub one-tenth micron wide beam at sample 222 for either modifying the sample 222 by ion milling, enhanced etch, material deposition, or for the purpose of imaging the sample 222. A charged particle multiplier 240 used for detecting secondary ion or electron emission for imaging is connected to signal processor 242, where the signal from charged particle multiplier 240 are amplified, converted into digital signals, and subjected to signal processing. The resulting digital signal is to display an image of sample 222 on the monitor 244.

A scanning electron microscope 241, along with power supply and control unit 245, is also provided with the FIB/SEM system 210. An electron beam 243 is emitted from a cathode 252 by applying voltage between cathode 252 and an anode 254. Electron beam 243 is focused to a fine spot by means of a condensing lens 256 and an objective lens 258. Electron beam 243 is scanned two-dimensionally on the specimen by means of a deflection coil 260. Operation of condensing lens 256, objective lens 258, and deflection coil 260 is controlled by power supply and control unit 245.

Electron beam 243 can be focused onto sample 222, which is on movable X-Y-Z stage 224 within lower chamber 226. Scanning electron microscope 241 produces a finely focused electron beam 243, which is scanned across the surface of the structure, preferably in a raster pattern. When the electrons in the electron beam 243 strike the surface of work piece 222, secondary electrons and backscattered electrons are emitted. Respectively, these electrons are detected by secondary electron detector 240 or backscattered electron detector 262. The analog signal produced either by secondary electron detector 240 or backscattered electron detector 262 is amplified and converted into a digital brightness value by signal processor unit 242. The resulting digital signal can be displayed as an image of sample 222 on the monitor 244.

A door 270 is opened for inserting sample 222 onto stage 224, which may be heated or cooled, and also for servicing an internal gas supply reservoir, if one is used. The door is interlocked so that it cannot be opened if the system is under vacuum. The high voltage power supply provides an appropriate acceleration voltage to electrodes in ion beam column 216 for energizing and focusing ion beam 218.

A gas delivery system 246 extends into lower chamber 226 for introducing and directing a gaseous vapor toward sample 222. A gas delivery system 246 is described in (9) U.S. Pat. No. 5,851,413 (issued Dec. 12, 1998) to Casella et al., "Gas delivery systems for particle beam processing," which is herein incorporated by reference in its entirety. Another gas delivery system is described in (10) U.S. Pat. No. 5,435,850 (issued Jul. 25, 1995) to Rasmussen, "Gas Injection System," which is also herein incorporated by reference in its entirety. For example, Dx gas can be delivered to enhance etching of a carbonaceous compound, or a metal organic compound can be delivered to deposit a metal.

System controller 219 controls the operations of the various parts of dual beam system 210. Through system controller 219, a user can cause ion beam 218 or electron beam 243 to be scanned in a desired manner through commands entered into a conventional user interface (not shown). System controller 219 can also comprise computer-readable memory 221 and may control dual beam system 210 in accordance with data or programmed instructions stored in memory 221. Computer aided design (CAD) data concerning the sample/semiconductor stored in memory 221 can be used to create a CAD polygon overlay or other positional data used to locate a feature of interest and alignment points or transfer fiducials as described above.

Apparatuses and systems described above may utilize high-accuracy beam placement method for local area navigation. Further, it should be recognized that elements, aspects or embodiments can be implemented via computer hardware or software, or a combination of both. Methods can be implemented in computer programs using standard programming techniques—including a computer-readable storage medium configured with a computer program, where the storage medium so configured causes a computer to operate in a specific and predefined manner—according to the methods and figures described in this specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, main-frames, workstations, networked or distributed computing environments, computer platforms separate, integral to, or in communication with charged particle tools or other imaging devices, and the like. Aspects may be implemented in machine readable code stored on a storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine readable code, or portions thereof, may be transmitted over a wired or wireless network. Implementations described herein may include these and other various types of computer-readable storage media when such media contain instructions or programs for implementing the steps described above in conjunction with a microprocessor or other data processor. Implementations may also include the computer itself when programmed according to the methods and techniques described herein.

Computer programs can be applied to input data to perform the functions described herein and thereby transform the input data to generate output data. The output information is applied to one or more output devices such as a display monitor. In some implementations, the transformed data may represent physical and tangible objects, including producing a particular visual depiction of the physical and tangible objects on a display.

As indicated, some implementations may also make use of a particle beam apparatus, such as a FIB or SEM, in order to image a sample using a beam of particles. Such particles used to image a sample may inherently interact with the sample resulting in some degree of physical transformation. Further, throughout the present specification, discussions utilizing terms such as "calculating," "determining," "measuring," "generating," "detecting," "forming," or the like, also refer to the action and processes of a computer system, or similar electronic device, that manipulates and transforms data represented as physical quantities within the computer system into other data similarly represented as physical quantities within the computer system or other information storage, transmission or display devices.

Particle beam systems suitable for carrying out implementations are commercially available, for example, from Thermo Fisher Scientific Company, the assignee of the present application. However, even though much of the previous description is directed toward the use of PFIB etching, milling, and deposition, the beam used to image or process the desired samples could comprise, for example, an electron beam, a laser beam, or a some other shaped ion beam, for example, from a liquid metal ion source, or another charged particle beam source. Further, although much of the previous description is directed at particle beam systems, implementations could be applied to any suitable sample control system employing a moveable sample stage to navigate to the location of a sample feature.

Although much of the previous description has application to modifying semiconductor wafers, implementations could be applied to any suitable substrate or surface. Further, whenever the terms "automatic," "automated," or similar terms are used herein, those terms will be understood to include manual initiation of the automatic or automated process or step. In the following discussion and in the claims, the terms "including" and "comprising" are used in an open-ended fashion, and thus should be interpreted to mean "including, but not limited to . . . ." The term "integrated circuit" refers to a set of electronic components and their interconnections (internal electrical circuit elements, collectively) that are patterned on the surface of a microchip. The term "semiconductor device" refers generically to an integrated circuit (IC), which may be integral to a semiconductor wafer, singulated from a wafer, or packaged for use on a circuit board. The term "FIB" or "focused ion beam" is used herein to refer to any collimated ion beam, including a beam focused by ion optics and shaped ion beams.

To the extent that any term is not specially defined in this specification, the intent is that the term is to be given its plain and ordinary meaning. The accompanying drawings are intended to aid in understanding the present invention and, unless otherwise indicated, are not drawn to scale.

The invention has broad applicability and can provide many benefits as described and shown in the examples above. Embodiments or implementations will vary depending upon the specific application, and not every embodiment or implementation will provide all of the benefits and meet all of the objectives that are achievable by the invention.

Although the present invention and its advantages have been described in detail, it should be understood that various changes, substitutions and alterations can be made to the embodiments or implementations described herein without departing from the spirit and scope of the invention as defined by the appended claims. Moreover, the scope of the present application is not intended to be limited to the particular embodiments or implementations of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments or implementations described herein may be utilized according to the present invention. Accordingly, the appended claims are intended to include within their scope such processes, machines, manufacture, compositions of matter, means, methods, or steps.

REFERENCES (1) L. A. Giannuzzi, F. A. Stevie, *Introduction to Focused Ion Beams: Instrumentation, Theory, Techniques, and Practice* (Springer, New York, 2005).
(2) J. Orloff, M. Utlaut, L. Swanson, *High Resolution Focused Ion Beams: FIB and Its Applications* (Kluwer Academic/Plenum Publishers, New York, 2003).
(3) U.S. Pat. No. 8,059,918 (issued Nov. 15, 2011) to Young et al., "High accuracy beam placement for local area navigation."
(4) U.S. Pat. No. 5,104,684 (issued Apr. 14, 1992) to Tao et al., "Ion beam induced deposition of metals."
(5) U.S. Pat. No. 5,958,799 (issued Sep. 28, 1999) to Russell et al., "Method for water vapor enhanced charged-particle-beam machining."
(6) U.S. Pat. No. 9,443,697 (issued Sep. 13, 2016) to Rue, "Low Energy Ion Beam Etch."
(7) U.S. Pat. No. 9,064,811 (issued Jun. 23, 2015) to Rue et al., "Precursor for planar deprocessing of semiconductor devices using a focused ion beam."
(8) U.S. Pat. No. 8,076,650 (issued Dec. 13, 2011) to Smith et al., "Multi-source plasma focused ion beam system."
(9) U.S. Pat. No. 5,851,413 (issued Dec. 22, 1998) to Casella et al., "Gas delivery systems for particle beam processing."
(10) U.S. Pat. No. 5,435,850 (issued Jul. 25, 1995) to Rasmussen, "Gas Injection System."

We claim as follows:

1. A method of chemically-enhanced charged particle beam milling of a work piece area, the method comprising:
    providing an etch-assisting gas to a surface of the work piece area targeted for milling, wherein at least a portion of the surface of the targeted work piece area consists essentially of carbonaceous material;
    directing a focused ion beam toward the portion of the surface that consists essentially of carbonaceous material, thereby removing carbon from the targeted area at a removal rate greater than a removal rate when no etch-assisting gas is used;
    in which:
        the etch-assisting gas comprises a chemical selected from a group consisting of methyl nitroacetate, methyl acetate, ethyl acetate, ethyl nitroacetate, propyl acetate, propyl nitroacetate, nitro ethyl acetate, methyl methoxyacetate, and methoxy acetylchloride; and
        the carbonaceous material is selected from the group consisting of diamond, vitreous carbon, polyimide material, and organic resin comprising other carbon-rich polymer material.

2. The method of claim 1 in which the focused ion beam originates from a plasma focused ion beam source.

3. The method of claim 1 in which ions of the focused ion beam are selected from the group consisting of: $Xe^+$, $Ar^+$, $Kr^+$, $O^+$, $O_2^+$, $N^+$, $N_2^+$, $NO^+$, and $NO_2^+$.

4. The method of claim 1 in which the focused ion beam operates during carbon removal at a very low or low acceleration voltage ranging from about 2 keV to about 14 keV.

5. The method of claim 1 in which the etch-assisting gas chemical is methyl nitroacetate.

6. The method of claim 1 in which the carbon-rich polymer material is selected from the group consisting of polycarbonate, polyester, polyethylene, polypropylene, polystyrene, and polyurethane.

7. A method of charged particle beam cleaning of a surface contaminated with hydrocarbon material, the method comprising:
    providing a carbon-removal precursor gas to a surface area targeted for cleaning;
    directing a charged particle beam toward the surface area targeted for cleaning, thereby removing hydrocarbon contaminant material from the surface at a removal rate greater than a removal rate when no carbon-removal precursor gas is used;
    in which:
        the carbon-removal precursor gas comprises a chemical selected from a group consisting of methyl nitroacetate, methyl acetate, ethyl acetate, ethyl nitroacetate, propyl acetate, propyl nitroacetate, nitro ethyl acetate, methyl methoxyacetate, and methoxy acetylchloride.

8. The method of claim 7 in which the charged particle beam is a focused ion beam.

9. The method of claim 8 in which the focused ion beam originates from a plasma focused ion beam source.

10. The method of claim 9 in which ions originating from the plasma focused ion beam source are selected from the group consisting of: Xe+, Ar+, Kr+, O+, O2+, N+, N2+, NO+, and NO2+.

11. The method of claim 9 in which the plasma focused ion beam operates during surface cleaning at an acceleration voltage ranging from about 2 keV to about 30 keV.

12. The method of claim 9 in which the plasma focused ion beam operates during surface cleaning at an acceleration voltage ranging from about 2 keV to about 5 keV.

13. The method of claim 12 in which ions originating from the plasma focused ion beam source are Xe+ ions.

* * * * *